United States Patent [19]
Pinkel

[11] Patent Number: 4,988,619
[45] Date of Patent: Jan. 29, 1991

[54] FLOW CYTOMETRY APPARATUS
[75] Inventor: Daniel Pinkel, Walnut Creek, Calif.
[73] Assignee: United States Department of Energy, Washington, D.C.
[21] Appl. No.: 126,153
[22] Filed: Nov. 30, 1987
[51] Int. Cl.[5] ............................................. C12Q 1/24
[52] U.S. Cl. ..................................... 435/30; 439/291; 439/39; 439/808; 356/39; 356/36; 356/72; 356/73
[58] Field of Search .................. 435/291, 808, 30, 34, 435/39; 356/39, 36, 72, 73

[56] References Cited

U.S. PATENT DOCUMENTS

| | | | |
|---|---|---|---|
| 3,084,591 | 4/1963 | Stevens. | |
| 3,710,933 | 1/1973 | Fulwyler et al. | |
| 3,785,735 | 1/1974 | Friedman et al. | 356/39 |
| 3,788,744 | 1/1974 | Friedman et al. | 356/39 |
| 3,871,770 | 3/1975 | Von Behrens et al. | 356/103 |
| 3,893,766 | 7/1975 | Hogg | 356/36 |
| 3,989,381 | 11/1976 | Fulwyler | 356/39 |
| 4,014,611 | 3/1977 | Simpson et al. | 356/72 |
| 4,280,623 | 7/1981 | Legorreta | 356/72 X |
| 4,325,706 | 4/1982 | Gershman. | |
| 4,408,877 | 10/1983 | Lindmo et al. | 356/38 |
| 4,522,494 | 6/1985 | Bonner | 356/39 |
| 4,660,971 | 4/1987 | Sage et al. | 356/73 X |

OTHER PUBLICATIONS

M. A. Van Dilla, Flow Cytometry: Instrumentation and Data Analysis, Academic Press, (1985), New York, pp. 1–8, 16, 77–128, 173–175, 223,232 and 233.

Primary Examiner—Christine Nucker
Assistant Examiner—Janelle D. Waack
Attorney, Agent, or Firm—Michael Lee; L. E. Carnahan; William R. Moser

[57] ABSTRACT

An obstruction across the flow chamber creates a one dimensional convergence of a sheath fluid. A passageway in the construction directs flat cells near to the area of one dimensional convergence in the sheath fluid to provide proper orientation of flat cells at fast rates.

14 Claims, 4 Drawing Sheets

FLOW CYTOMETRY APPARATUS

BACKGROUND OF THE INVENTION

The U.S. Government has rights in this invention pursuant to Contract No. W-7405-ENG-48 between the U.S. Department of Energy and the University of Calif., for the operation of Lawrence Livermore National Laboratory.

Flow cytometers/sorters have been developed over the last few decades to automate the counting or separation of body tissue cells and organelles in aqueous suspension. An important part of every flow cytometer/sorter is its flow chamber. It must be designed to have satisfactory hydrodynamic, optical, mechanical, and electrical characteristics. To obtain accurate measurements it is important that all the particles pass through the region of uniform sensitivity of the sensors. This is accomplished using a method called hydrodynamic focusing. In hydrodynamic focusing a flow of "sheath" fluid is established through a constricting nozzle. The suspension of sample particles is introduced into the sheath fluid from a small tube (sample tube) and is carried along a streamline of the sheath flow in the flow direction.

In the measuring or sorting of certain flat cells such as sperm cells, it is important that the cells are properly oriented. In the past, properly orienting certain flat cells has been inefficient and slow. In the prior art, flow chambers with a slotted nozzle orifice, or wedge shaped sample tubes are used to orient flat cells. The prior art is discussed more fully in "Flow Cytometry: Instrumentation and Data Analysis," edited by Marvin A. Van Dilla, Phillip N. Dean, Ole D. Laerum, and Myron R. Melamed, Academic Press Inc. 1985, incorporated herein by reference.

This invention relates to a method and apparatus for orienting certain flat cells. The advantage of this invention is its ability to achieve adequate cell orientation at much higher sample measurement rates.

SUMMARY OF THE INVENTION

An object of the invention is to more efficiently measure or sort flat cells.

Another object is to more quickly measure or sort flat cells.

Another object is to more accurately measure or sort flat cells.

Another object is to properly orient flat cells in a cell flow cytometer/sorter.

Another object is to properly orient flat cells supplied at a faster flow rate.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

The invention is a method or apparatus for orienting flat cells which comprises: a tubular flow o chamber through which a sheath fluid flows in a flow direction; an obstruction which causes the sheath fluid flow to converge in one dimension; and means for directing the flat cells in a sample fluid near to the area of the one dimensional convergence in the sheath fluid, which orients the flat cells.

BRIEF DESCRIPTION OF THE DRAWINGS

The accompanying drawings, which are incorporated and form a part of the specification, illustrate embodiments of the invention and, together with the description, serve to explain the principles of the invention.

DESCRIPTIONS OF THE PREFERRED EMBODIMENTS

Figure 1:
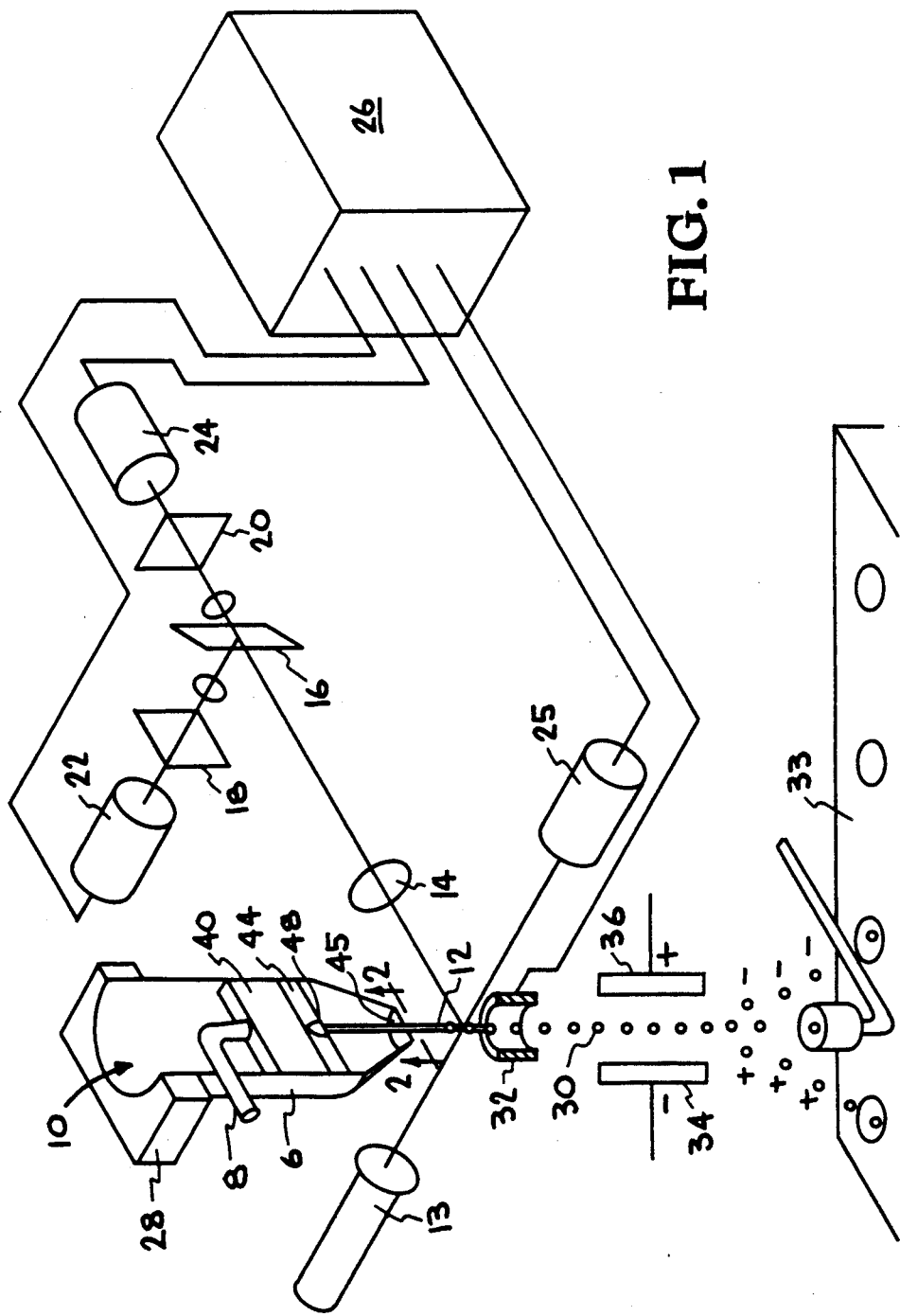
FIG. 1 is a schematic drawing of a flow sorter with one embodiment of the invention.

There are many different cell flow cytometer/sorters. FIG. 1 shows a schematic view of one type of cell flow sorter with the invention. Flat cells, which may be stained with one or more fluorescent dyes, enter the flow chamber 6 through sample tube 8. A sheath fluid is also introduced into the flow chamber through an entrance 10. The flat cells are carried in single file in the sheath fluid stream 12 through a focussed laser beam from laser 13 whose wavelength is adjusted to excite a fluorescent dye that may be present. Some of the fluorescence and/or light scatter produced during the laser beam crossing is focused by an objective lens 14 onto a beam splitter 16 and projected through spectral filters 18 and 20 onto photomultipliers 22 and 24. The photomultipliers 22 and 24 convert the fluorescence and/or light scatter to electrical pulses whose amplitudes are proportional to the total light reaching the photomultipliers. Similarly, a photomultiplier or a photodiode 25 detects fluoresence or scatter in the direction along the laser beam. The electrical pulses are sent to an electrical signal processor 26. Flat cells to be sorted are recognized by their distinctive fluorescence and/or light scatter intensities. After measurement, each flat cell flows in the sheath fluid stream 12 until it reaches the point where the stream 12 breaks into discrete droplets 30. A piezoelectric transducer 28 vibrates the flow chamber 6 causing the stream 12 to break into the discrete droplets 30. At the point where the stream 12 breaks into droplets 30, a charging collar 32 controlled by the electrical signal processor, induces an electrical charge on each droplet containing a flat cell to be sorted. The droplets fall through a high electrostatic field where the charged droplets are deflected and collected by collector apparatus 33. The electrostatic field is produced by deflection plates 34 and 36.

Figure 2:
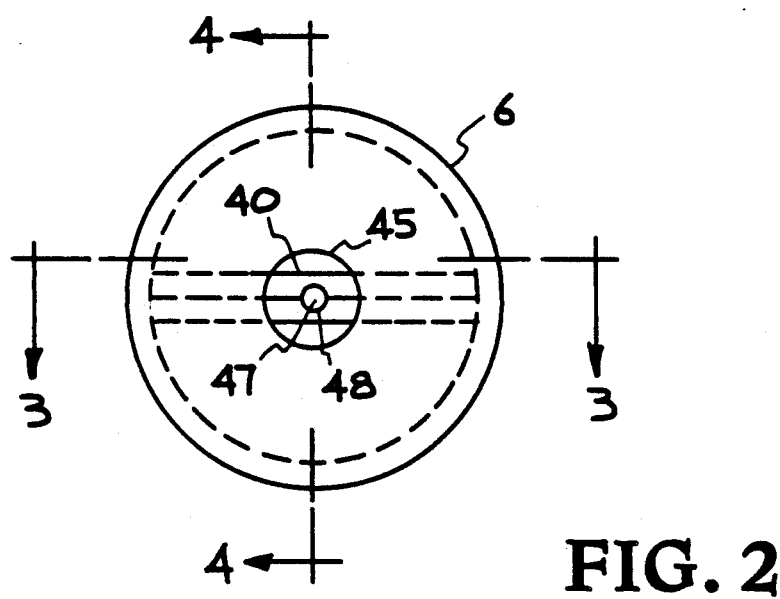
FIG. 2 is a cross sectional and enlarged view of the flow chamber along section 2—2.
Figure 3:
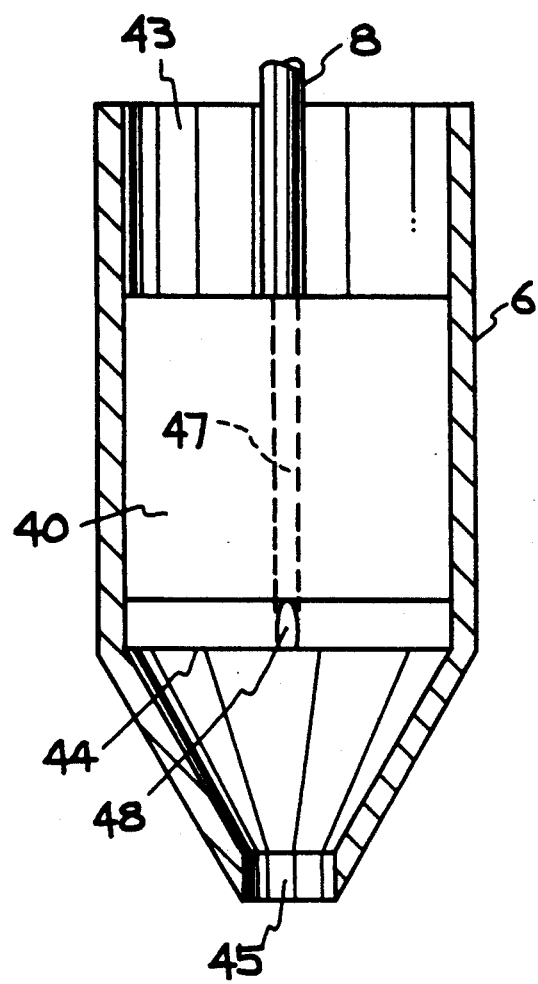
FIG. 3 is another cross sectional view of the flow chamber along section 3—3.
Figure 4:
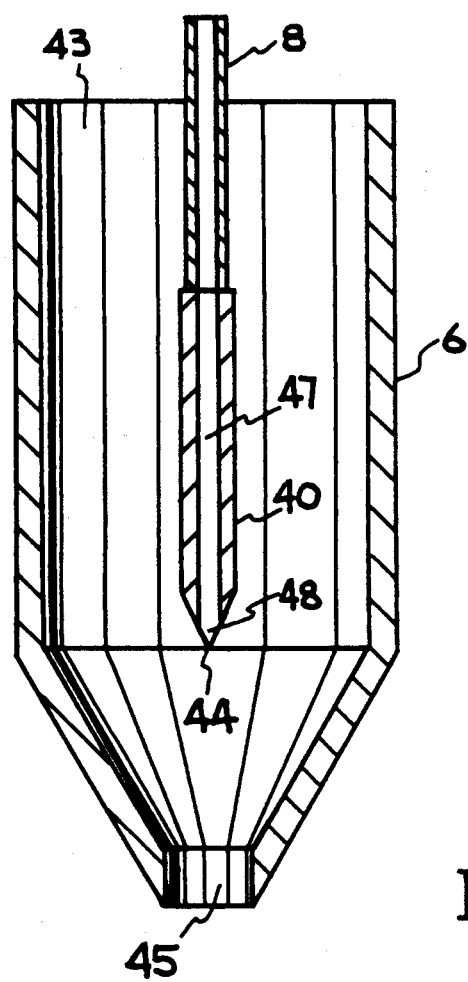
FIG. 4 is another cross sectional view of the flow chamber along section 4—4.

FIG. 2 is a cross sectional view of the tubular flow chamber along section 2—2 in FIG. 1, showing an embodiment of the invention. FIG. 3 is a cross sectional view of FIG. 2 along section 3—3. FIGS. 2 and 3 show a fin 40, which is a flat solid extending across the diameter of the flow chamber. Sample tube 8 extends through the flow chamber to the fin where it is in fluid connection with a passageway 47 which passes near to the center of fin 40 as shown. The fin is beveled to an edge 44 as shown in FIG. 4. The fin may have other possible shapes as long as they do not introduce turbulence into the fluid flow. The flat cells in a sample fluid flow through sample tube 8 to passageway 47 which terminates at aperture 48 where the sample fluid enters the sheath fluid area. The shape of the aperture 48 is created by the cross section of the passageway 47 and the bevel of the fin. The aperture 48 has a circular cross-section as shown in FIG. 2. Therefore the length of the cross-section of the aperture 48 is substantially less than or equal to the thickness of the fin 40.

The sheath fluid flows through the flow chamber in a flow direction from opening 43 to exit 45, and part of fin 40 is upstream of the position where the flat cells enter the sheath fluid area. Part of fin 40 may extend downstream from the aperture 48. The beveled fin 40, which lies along a plane that is parallel to the central axis of the flow chamber, causes the sheath fluid to converge in one dimension at its downstream edge, which causes the flat cells to orient themselves in the plane of convergence.

Figure 5:
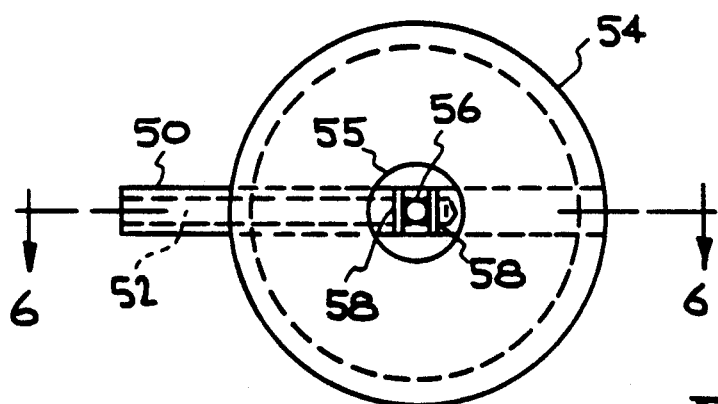
FIG. 5 is a cross sectional view of flow chamber of another embodiment of the invention.
Figure 6:
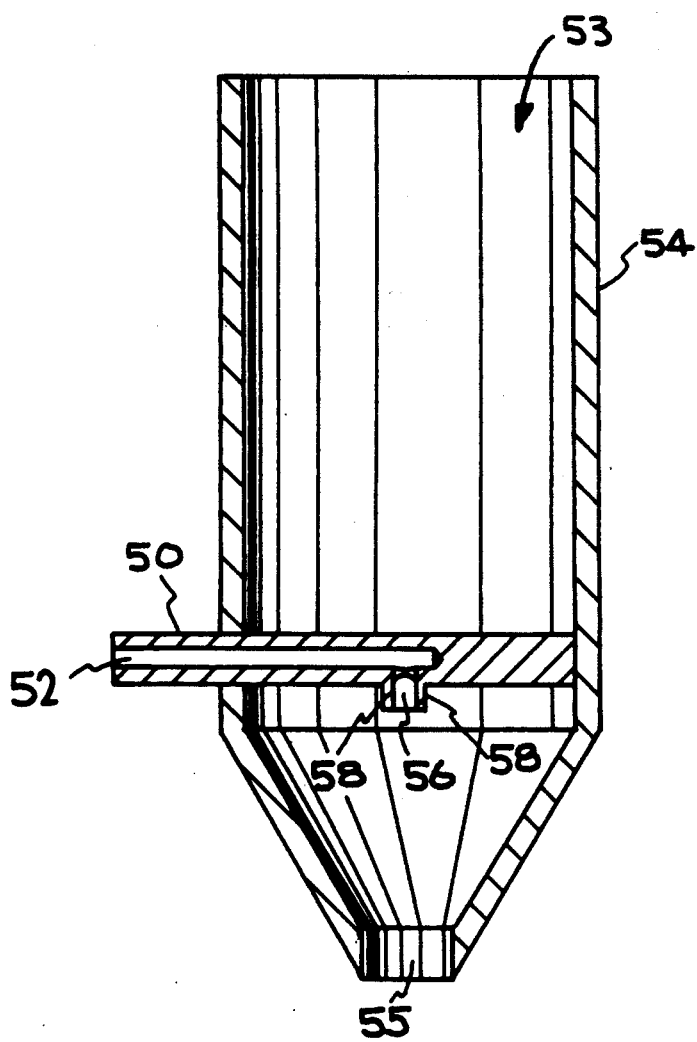
FIG. 6 is another cross sectional view of the flow chamber as shown in FIG. 5 along section 6—6.

FIGS. 5 and 6 are illustrations of another embodiment of the invention. In this embodiment a cylindrical rod 50 is used to create the streamline convergence in one dimension. The obstruction of rod 50 is perpendicular to the axis of the flow chamber 54, and the rod extends across the diameter of the flow chamber 54. In this embodiment the passageway 52 inside rod 50 directs the sample fluid to aperture 56, where the sample fluid is released into the sheath fluid. The sheath fluid flows through the flow chamber from opening 53 to exit 55. The obstruction 50 creates a convergence in one dimension along the length of the obstruction. The obstruction 50 is upstream from where the flat cells enter the sheath fluid at aperture 56 and positioned to cause the flat cells to pass through part of the convergence in one dimension, thus orienting the flat cells. Fins 58 are located near this aperture to limit the lateral diffusion of the sample fluid on the downstream side of the obstruction 50 before the sample fluid enters the sheath flow. The aperture 56 has a circular cross-section as shown in FIG. 5. Therefore the length of the cross-section of the aperture 56 is substantially less than or equal to the diameter of the cylindrical rod 50.

The foregoing description of preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for orienting cells in a sheath fluid in a cytometer/sorter, comprising:
   a flow chamber;
   means for flowing the sheath fluid through the flow chamber along a direction of flow;
   means for obstructing the flow of the sheath fluid in the flow chamber with a first dimension, which extends substantially across the flow chamber and is substantially perpendicular to the direction of flow and with a thickness perpendicular to the first dimension of the obstructing means wherein the sheath fluid flows around the thickness so that the sheath fluid converges in only one dimension at the downstream edge of the means for obstructing; and
   means for introducing the cells through the means for obstructing the flow to the region where the sheath fluid converges in only one dimension in the sheath fluid to orient the cells, with an aperture wherein as the cells pass from the means for introducing the cells to the region where the sheath fluid converges the cells pass through the aperture with a cross-sectional length substantially less than or equal to the thickness of the means for obstructing the flow.

2. An apparatus, as recited in claim 1, wherein the means for obstructing the flow comprises a fin.

3. An apparatus, as recited in claim 2, wherein part of the fin is substantially flat.

4. An apparatus, as recited in claim 3, wherein a portion of the flat part of the fin lies along a plane that is substantially parallel to the flow direction of the flow chamber and extends substantially across a diameter of the flow chamber.

5. An apparatus, as recited in claim 4, wherein the portion of the fin which is furthest down stream is beveled.

6. An apparatus, as recited in claim 5, wherein the means for introducing cells comprises a tube and a passageway through the fin connected to the tube and an aperture where the passageway exits the fin.

7. An apparatus, as recited in claim 1, wherein the means for obstructing is a rod with a length extending substantially from one side of the flow chamber to an opposite side of the flow chamber.

8. An apparatus, as recited in claim 7, wherein the means for introducing cells comprises a passageway along part of the length of the rod, which terminates at a passageway aperture.

9. A method for orienting flat cells in a sheath fluid in a flow cytometer/sorter, comprising the steps of:
   flowing the sheath fluid through a flow chamber;
   obstructing the sheath fluid flow with an obstruction wherein the obstruction has a first dimension, which extends substantially across the flow chamber and is substantially perpendicular to the flow of the sheath fluid and with a thickness substantially perpendicular to the first dimension of the obstruction wherein the sheath fluid flows around the thickness of the obstruction so that flow directions of the sheath fluid converge in only one dimension at the downstream edge of the obstruction; and
   introducing the flat cells through the obstruction and through an aperture to the region where the flow directions of the sheath fluid converges in only one dimension thus orienting the cells, wherein the length of the aperture is substantially less than or equal to the thickness of the obstruction.

10. A method, as recited in claim 9, wherein the step of obstructing the sheath fluid comprises the step of directing the sheath fluid past a flat fin.

11. A method, as recited in claim 10, wherein step of introducing the flat cells, comprises the steps of:
   directing the cells into a tube;
   directing the cells into a passageway in the fin that is in fluid connection with the tube; and
   directing the cells through an aperture in the fin connected to the passageway with the aperture being downstream from part of the flat fin.

12. A method, as recited in claim 9, wherein the step of obstructing the sheath fluid comprises the step of directing the sheath fluid past a rod extending substantially across a diameter of the flow chamber.

13. A method, as recited in claim 12, wherein the step of introducing the flat cells, comprises the steps of:
   directing the cells into a passageway in the rod; and
   directing the cells through an aperture in the rod connected to the passageway with the aperture being downstream from part of the rod.

14. An apparatus for orienting cells in a sheath fluid in a flow cytometer/sorter, comprising:
   a flow chamber;
   means for flowing the sheath fluid through the flow chamber along a direction of flow;
   means for obstructing the flow of the sheath fluid in the flow chamber so that the sheath fluid converges in only one dimension, wherein the means for obstructing is a rod with a length extending substantially from one side of the flow chamber to an opposite side of the flow chamber;
   means for directing the cells to the region where the sheath fluid converges in only one dimension in the sheath fluid to orient the cells, wherein the means for directing cells comprises a passageway along part of the length of the rod, which terminates at a passageway aperture; and
   fins oriented parallel to the flow direction of the sheath fluid, the fins being positioned on each side of the passageway aperture.

* * * * *